(12) United States Patent
Suhonen

(10) Patent No.: US 6,854,974 B1
(45) Date of Patent: Feb. 15, 2005

(54) DEVICE FOR RESTORATIVE DENTISTRY

(76) Inventor: Jouko Suhonen, 663 Garth Ct., Yorktown Heights, NY (US) 10598

( * ) Notice: Subject to any disclaimer, the term of this patent is extended or adjusted under 35 U.S.C. 154(b) by 0 days.

(21) Appl. No.: 09/913,833

(22) PCT Filed: Feb. 18, 2000

(86) PCT No.: PCT/FI00/00126
§ 371 (c)(1),
(2), (4) Date: Dec. 3, 2001

(87) PCT Pub. No.: WO00/49962
PCT Pub. Date: Aug. 31, 2000

(30) Foreign Application Priority Data

Feb. 22, 1999  (FI) .................................................. 990372

(51) Int. Cl.[7] .............................................. A61C 5/04
(52) U.S. Cl. ............................. 433/226; 433/80; 433/89
(58) Field of Search .............................. 433/226, 228.1, 433/80, 81, 89, 90

(56) References Cited

U.S. PATENT DOCUMENTS

| | | | | |
|---|---|---|---|---|
| 404,745 A | * | 6/1889 | Taylor ........................ | 433/226 |
| 1,341,736 A | * | 3/1920 | Cruttenden ................... | 433/89 |
| 1,637,153 A | * | 7/1927 | Lawton ........................ | 401/34 |
| 3,942,539 A | * | 3/1976 | Corliss et al. .............. | 132/286 |
| 4,411,623 A | * | 10/1983 | Axelsson ...................... | 433/80 |
| 5,246,371 A | * | 9/1993 | Fischer ....................... | 433/217.1 |
| 5,330,357 A | * | 7/1994 | Keller ........................ | 433/215 |
| 5,816,805 A | * | 10/1998 | Cheetham ..................... | 433/90 |
| 6,007,334 A | * | 12/1999 | Suhonen ....................... | 433/39 |

FOREIGN PATENT DOCUMENTS

| | | |
|---|---|---|
| DE | 4011568 | 10/1991 |
| DE | 0572947 | 12/1993 |

* cited by examiner

Primary Examiner—John J Wilson
(74) Attorney, Agent, or Firm—Connolly, Bove, Lodge & Hutz LLP

(57) ABSTRACT

A device for filling and reinforcing an internal tunnel preparation in a tooth in which the approximal margin is kept as short as possible in order to prevent overhangs. The device includes a closed first elongate and flexible container means having one end provided with a tip or string to enable insertion of the first container means into an interdental space adjacent the portion of said tooth, from which approximal caries has been removed. The first container means is filled or fillable with a flowable restorative material, which is intended to flow into and fill the tunnel preparation as soon as a hole has been punched into the flat container means.

29 Claims, 4 Drawing Sheets

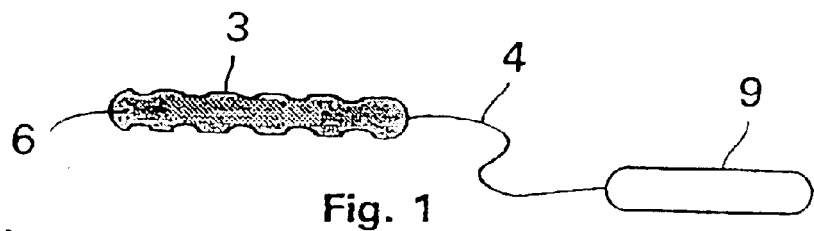
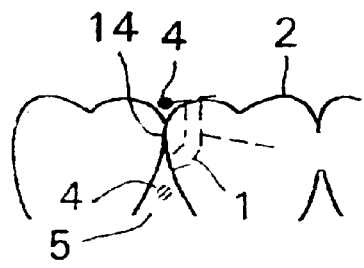
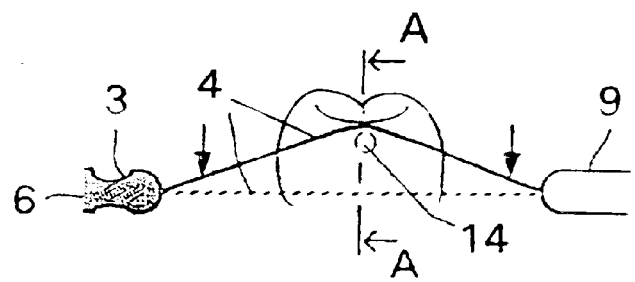
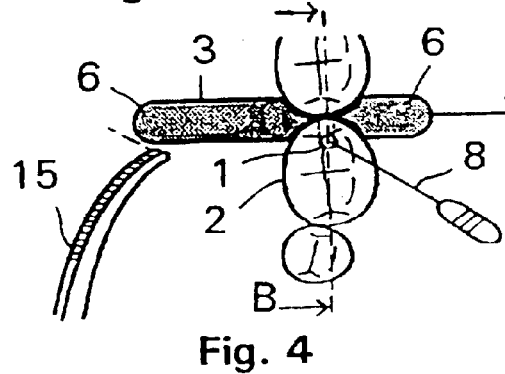
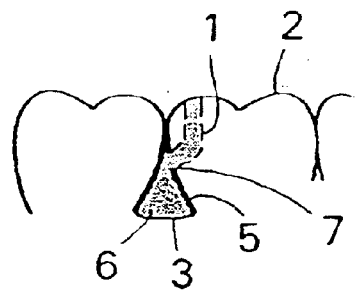
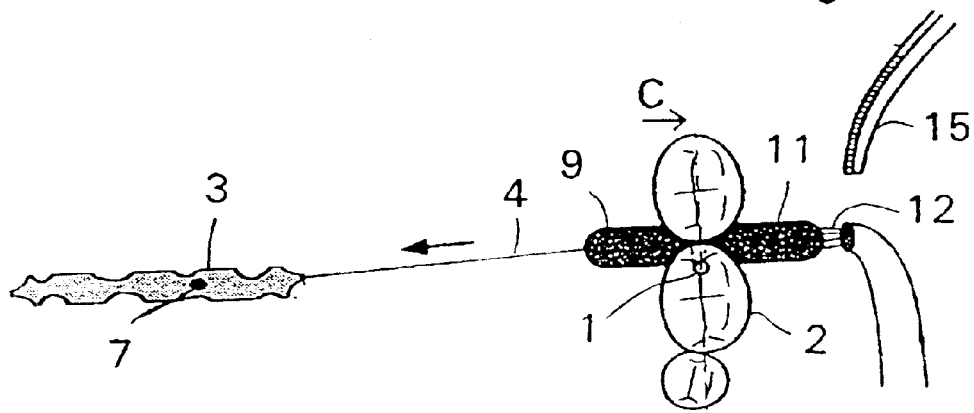
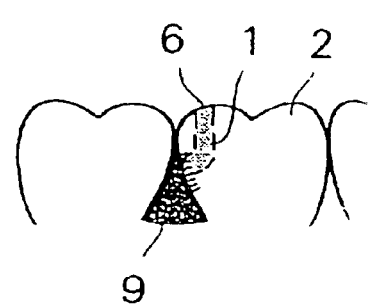

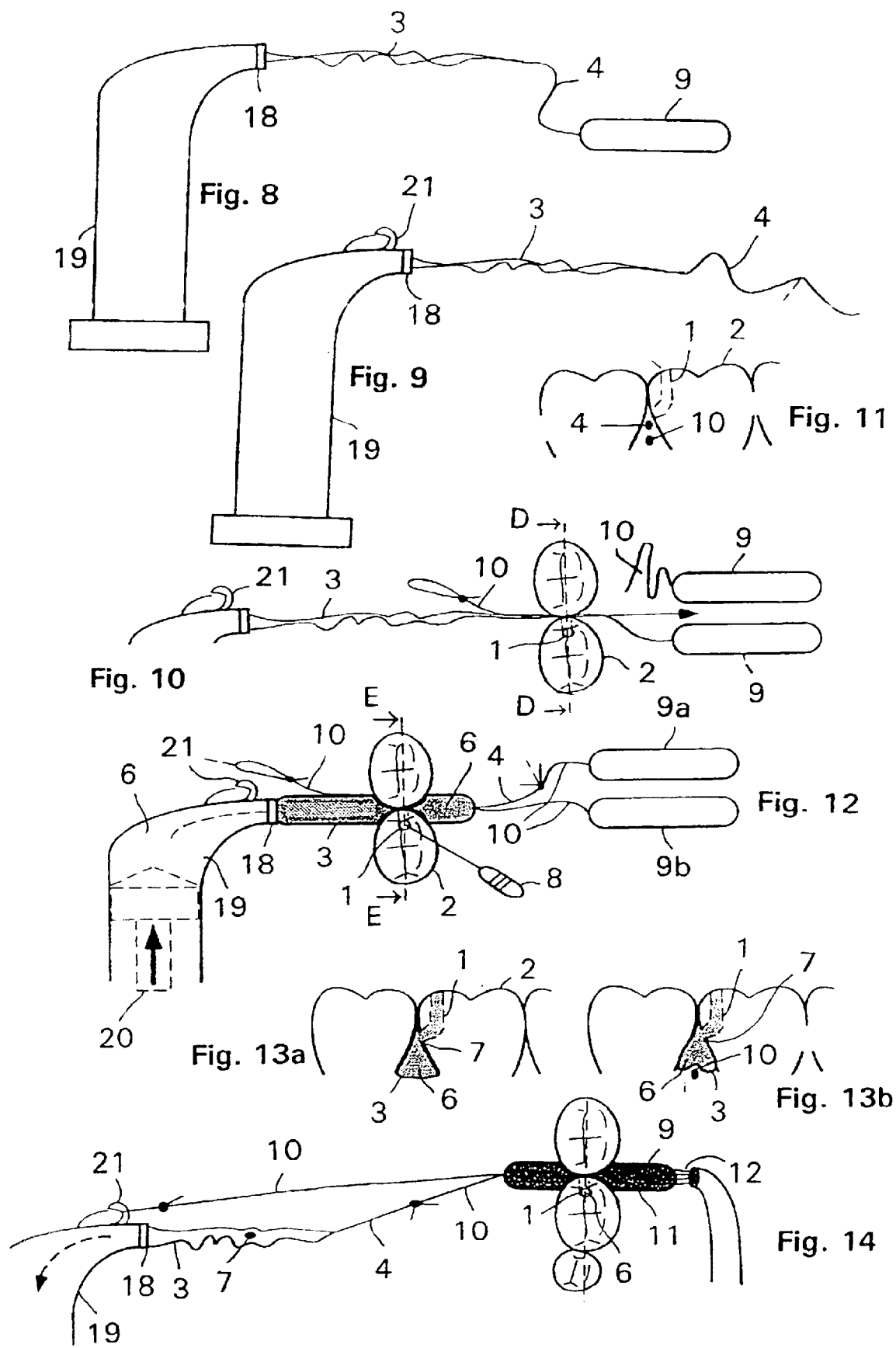

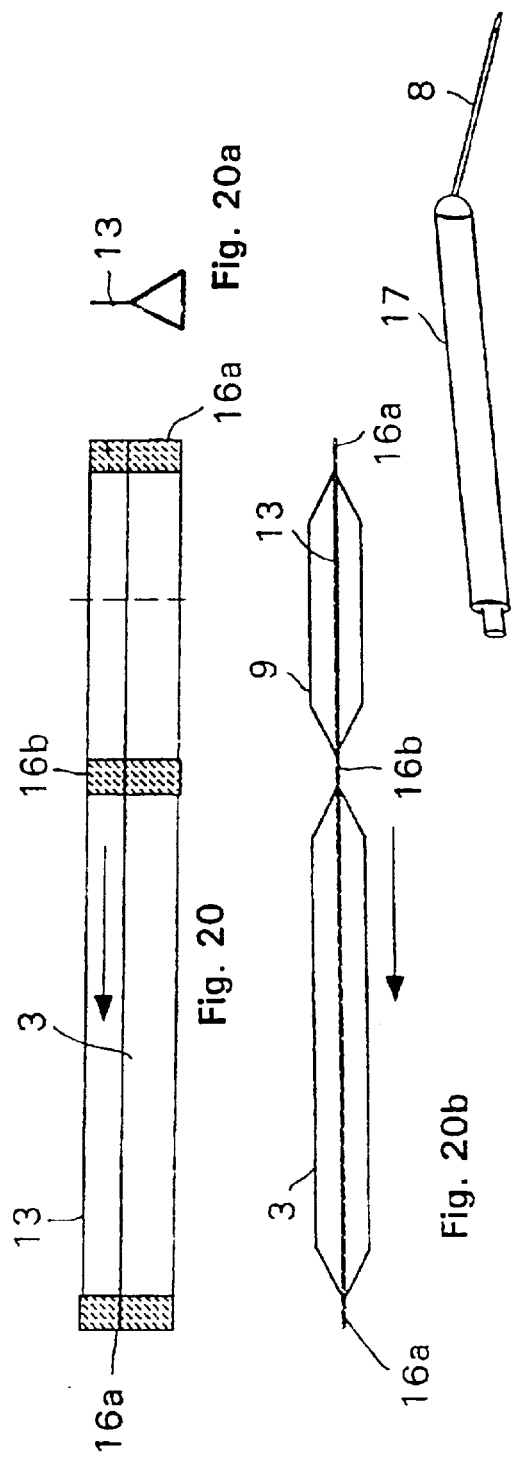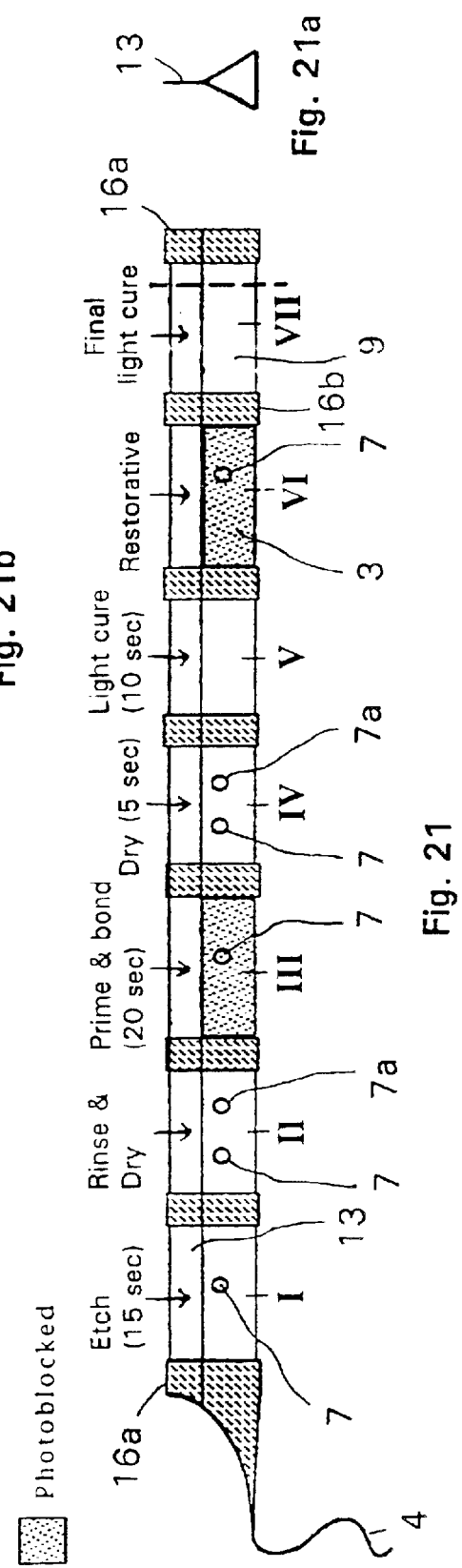

DEVICE FOR RESTORATIVE DENTISTRY

This invention concerns a device for filling and reinforcing an internal tunnel in a tooth from which tooth approximal caries has been removed by means of a tunnel preparation and for preventing overhangs.

When human teeth are damaged through demineralisation process caused by bacterial acid attacks this occurs practically always on very specific tooth sites which have been colonized by cariogenic micro-organisms. Interproximal and occlusal tooth surfaces are the main colonization sites of aciduric and acidogenic mutans streptococci which are the main causative bacteria of human dental caries.

Matrix bands made of metal or cellulose acetate and interdental wedges made of limited adaptable wood or nonadaptable plastic have been traditionally used as aids to restore cavities prepared into caries affected teeth according to G. V. Black's principles Today's modern primary cavity management considers these aids and principles as obsolete, since they are absolutely too invasive, destructive and even problem creating. The technology of tooth restoration has definitively changed from macro- to microconservative management of the decay. It is no more necessary to extend the cavities for prevention since cariostatic restorative materials, such as fluoride releasing glass ionomers, are available. Also extension for retention is not necessary since adhesive restorative materials, such as composite resins, glass ionomers and compomers, can be bonded to tooth hard substances, enamel and dentin.

With increasing concerns about microleakage and possibility of overfilling, as far macroconservative management of large cavities treated with conventional Class II composite resin restorations and inlays is concerned, there is a desire to cut down especially on gum related approximal and marginal perimeter of restorations. The shorter the margin of the cavity preparation, the less the potential for marginal breakdown, leakage and overfilling. Handling of composite resin and glass ionomer materials in conventional box like or round bevel shaped approximal cavity preparations is not easy, since these materials tend to "over flow" to overhangs below the gum line which then serve as niches for facultative anaerobic gram-negative flora to colonize. Several recent studies have shown that the type of oral microflora, which causes chronic periodontal infections, often accompanied with uneven vertical bone loss at the affected tooth site, also spreads out during episodes of dental bacteremia to heart and other organs clogging arterias. This triggers severe health conditions, such as coronary heart diseases, strokes and is also associated with pre-term low birthweight infants (Mattila et al. 1989, Syrjänen 1990, DeStefano et al. 1993, Beck et al. 1996, Joshipura et al. 1996, Herzberg & Meyer 1996, Scannapieco & Mylotte 1996, Grossman et al. 1997, Dasanayake 1997, Curtis 1997). When gums become inflamed due to contact with a marginal foreign body (overfilled restoration) and on it growing bacterial plaque, gingival sulcus is lined by an ulcerated epithelium. Capillaries beneath such an epithelium bleed spontaneously even after passage of food or a toothbrush over the gingival margin and allow different bacterial species to enter and survive in the bloodstream. Alone stroke incidence in the U.S. is dramatically higher than once thought. Some 700.000 occur each year, 40% more than previously estimated (Time magazine's citation from Journal of the American Medical Association and Stroke, 1998). It seems clear that overhangs/overfillings of dental restorations, which maintain chronic periodontal inflammation breaching the mucosal lining are by all means to be avoided, then even normally harmless streptococci as commensals of the normal oral flora behave as thrombogenic agent after having encountered platelets in bloodstream (Herzberg 1996).

Further conserns in conventional approximal cavity management, in which the marginal ridge has been removed to get access to the carious lesion, is the fact that direct composite resin restorations do not warrant stable contact points. This is due to difficulty to manipulate sticky or flowable composite material to tight contacts to the adjacent teeth. Open approximal contacts lead to food impaction and retention. This forsters plaque accumulation and makes its removal difficult which within a short time causes inflammation of the dental papilla, i.e. the gum part between two adjacent teeth, and marginal gingiva. Consequent gingival pocket formation and bleeding due to food impaction contributes to dental bacteremia. Also proximal wear of composites generally questions the feasibility of their use in contact areas (Ziemiecki et al. 1992; Wendt et al. 1996).

The primary role of the restorative dentistry should be to restore what has been lost by the very disease itself and to preserve as much as possible of the remaining hard tissue, of intact enamel and dentin. As the initial carious lesion occurs underneath the contact point, underneath the marginal ridge, there is no need to destroy the contact point and the ridge to get access to carious lesion. Tooth's marginal ridge should by all means be preserved to ensure a stable approximal contact.

The understanding complex relationships had led to more accurate dental care. The need for operative treatment of approximal carious lesions depends on whether or not caries process has reached the dentin. The sensitivity of dental radio-graphs, i.e. the ability to correctly diagnose, for detecting interproximal caries was earlier reported to be 59.4% (Douglass et al. 1986). Cavity detection in approximal tooth surfaces by means of digital images, e.g. by using storage phosphor system, opens new possibilities to determine that very condition/"moment" when an early caries lesion has penetrated into dentin and a primary restoration is indicated, more accurately (Wenzel et al. 1991, Nielsen et al 1996, Svanaes et al. 1996). It is of importance to choose a restoration procedure that allows a simple and complete access to the lesion without destroying the tooth's own natural and stable contact point which practically is never affected by initial caries. The filling procedure itself should be chosen so that no new problems, such as marginal breakdown, microleakage and/or overfilling are created, which would have health hazardous consequences.

Since widely used conventional tooth restoring procedures are unnecessarily radical, extensive and complex, simpler procedures have been sought. Microconservative "internal tunnel" preparation as described by Jinks 1963 as well by both Hunt and Kent independently 1984, presents a very sophisticated method to treat the carious proximal lesion without loosing the important natural contact point between two adjacent teeth. From the occlusal approach a small round bur is passed down starting through central main fissure until the dentinal "approximal" lesion which can be easily identified in the inside of the tooth as a dark brown/black stripe and/or by probe which sticks. As the dentin caries has been removed, the overlying porous enamel, through which the initial lesion has passed into dentin, can easily be identified as demineralized enamel and punched-out.

To ensure complete caries removal without weakening the marginal ridge unnecessarily, tunnel preparations are performed using extra fine instruments, preferably under an operating microscope similar to endodontic treatments. The operating microscope allows better visualization of the working field, ensuring that the caries process inside of the tooth is more readily inspected with bright illumination and magnification. The principles of microsurgery in restorative dentistry are relatively new and allow the clinician to perform the treatment so that the strength of the prepared tooth remains 92% and more of the sound value (Hill & Halaseh 1988).

No doubt the ability of filling materials (also called cements, i.e. syntetic analogues for enamel and dentin) to support the marginal ridge with an underneath preparation increases as the diameter of the tunnel itself decreases. Tunnel cavities have been filled by introducing kneadable, low viscous or flowable restoration materials from the occlusal approach using conventional hand instrumental application of injection. To fill such a cavity of a small diameter through one opening, especially if the air escape is not optimally provided, is difficult, if not impossible. Indeed by conventional "orthograde" filling access air will be clogged in the cavity since the other end of the tunnel is closed by a matrix band. Air cushion hinders and impedes the complete filling of the tunnel. To gain maximal reinforcing and maximal strength of the restored tooth, it is of importance to fill the tunnel completely and bubble-free with an adhering material.

Glass ionomer cements, composite resins and their mixtures, also called compomers, are for the moment the materials of choice to restore tunnel preparations. It has been shown that a proper filling of a tunnel cavity with glass ionomer, the undermined marginal ridge can be considered reinforced and fracture susceptibility of the area is eliminated (Hill & Halaseh 1988). To prevent recurrent caries of the operated area, glass ionomer or other fluoride leaching or anti-mutans streptococci-agent containing/releasing materials are preferably to be used. It has been reported that composite resin materials containing Ag+ (silver) fillers or Apacider-fillers (Ag, Zn) or other antibacterial fillers hinder the growth of mutans streptococci (Yamamoto et al. 1996, Syafiuddin et al. 1997) and so reduce recurrent caries of the primarily treated area.

Whichever filling materials and devices are used, it is of utmost importance to have a proper control of the procedure. Two important characteristics which cause failures in conventional tunnel restorations when filled from occlusal approach are:

1) Incomplete filling. Since visual control and air escape are not provided. There is no way to ensure the tunnel is filled completely until the very end. Use of injection cannulas does not solve this problem, since they cannot be pushed through the entire tunnel system. Cannulas are also too thick, since they have to have a certain diameter to be able to pass the viscous filling material.

2) Overfilling. There is no visual control over concave tooth contours which may cause leakage under a conventional matrix band The object of the present invention is to eliminate the above problems, which is achieved with a device according to the characterizing part of claim 1.

By means of this device an internal tunnel cavity can be filled and reinforced with a flowable restorative material e.g. an adhering synthetic filling material from approximal access, i.e. retrograde filling, while air escape from the tunnel cavity through an uncovered occlusal opening of said tunnel is guaranteed. A first flexible container means acts as a special interdental device and releases flowable restorative or filling material into the tunnel cavity from the approximal access.

According to a prefered embodyment the device is further provided with a second flexible container device, attached or attachable to the first flexible container device by means of a string, which second container device is aimed to be used for sealing the approximal cavity perimeter, which may be very short, during a curing phase of the restorative material, as soon as the filling of the entire tunnel cavity has been completed.

Below the device according to the present invention will be described in more detail, with reference to the drawings, wherein FIG. 1 shows a schematic side view of a prefered embodiment of the device;

FIG. 2 shows a first and a second stage in inserting a device shown in FIG. 1 into an interdental space;

FIG. 3 shows a cross section A—A in FIG. 2;

FIG. 4 shows a top view of a stage where a first container means of the device has been pulled into the interdental space;

FIG. 5 shows a cross section B—B in FIG. 4 at a stage when the tunnel preparation has been completely filled with a flowable restorative material;

FIG. 6 shows a top view of a stage of light curing the restorative material with a second container means of the device pulled into the interdental space;

FIG. 7 shows a cross section C—C in FIG. 6 during the light curing;

FIG. 8 shows a side view of a second embodiment of a device according to the invention;

FIG. 9 shows a side view of a third embodiment of a device according to the invention;

FIG. 10 shows a first stage of two alternative ways to insert a device shown in FIG. 9 into an interdental space;

FIG. 11 shows a cross section D—D in FIG. 10 according to one of the alternatives, FIG. 12 shows a top view of a stage where the first container means of the device shown in FIG. 9 has been pulled into the interdental space according to the both alternatives;

FIGS. 13a and 13b show a cross section E—E according to the first and the second alternative, respectively when the tunnel preparation has been filled with the flowable restorative material;

FIG. 14 shows a stage where the second container means has been pulled into the interdental space and light curing of the restorative material is carried out;

Figure 15:
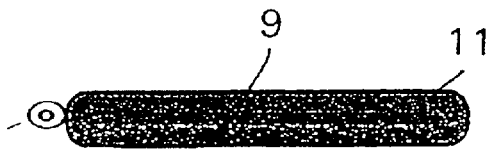
FIGS. 15 and 16 show two alternative embodiments of the second container means filled with a photoluminicencing medium.
Figure 16:
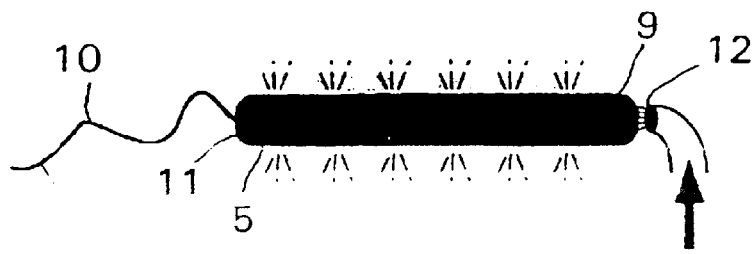
Figure 17:
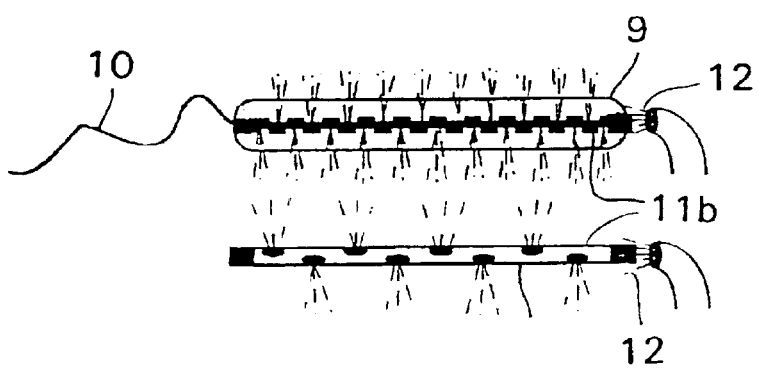
FIG. 17 shows a further embodiment of the second container means provided with a flexible, transversally illuminating fiber optic, and an alternative embodiment of such a fiber optic.
Figure 18A:
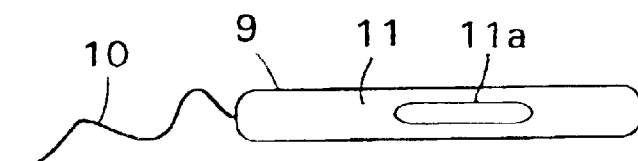
Figure 18B:
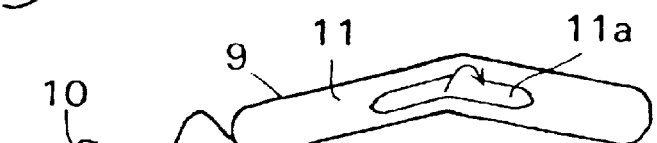
Figure 18C:
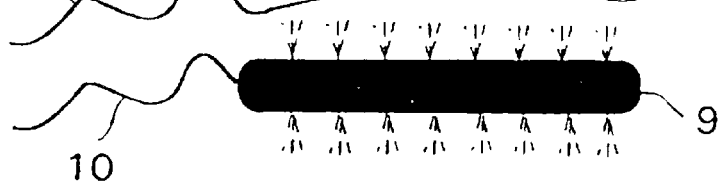
Figure 19:
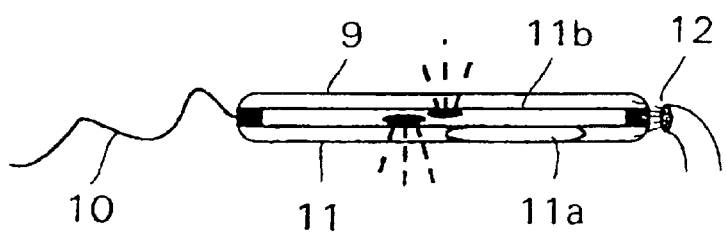

FIGS. 18a–c show still a further emodiment of the second container means,

FIG. 19 shows an embodiment of the second container means provided with a combination of chemiluminicence and fiber optic.

FIGS. 20, 20a and 20b show front, side, and end views of a further emodiment of a device according to the invention, FIGS. 21 and 21a show a further prefered embodiment of the device according to the invention, i.e. a multi functional device.

FIG. 21b shows a 3-way syringe used in the invention.

The device comprises a closed first elongate and flexible container means 3 having on end provided with a tip or sting 4 to enable insertion of said first container means 3 into an interdental space 5 adjacent a portion of a tooth 2 from which approximal caries has been removed. The first container means 3 is prefilled or fillable with a flowable restorative material 6, i.e. an adhering synthetic filling material, which may be self, dual, chemically or light curable. The restorative material is intended to flow into and fill a tunnel preparation 1 extending through the tooth 2 as an occlusal access preparation from the center fissure of the tooth 2 to said interdental space 5. A hole 7 is intended to be punched into said first container means 3 for instance by means of a needle 8 brought into contact with the first container means through said tunnel preparation 1. A hemostat 15 can be used to squeeze and wrap the first container means 3 in order to force the restorative material 6 into the tunnel preparation 1.

According to a prefered embodiment the first container means 3 is prefilled to about 60 to 80% of its volume with the flowable restorative material. This enables the first container means 3 to be easily pulled into the interdental space 5 whereby the container means 3 simultaneously will be constricted by the contacting teeth.

In order to effectively prevent overhangs a second closed and flexible container means 9 is attached or attachable to the device. According to a first prefered embodiment the second container means 9 is attached or attachable to the tip or string 4 of the first container means 3. If the string 4 of the first container means is stationary connected to the second container means 9 as shown in FIG. 1 a first step in inserting the device into the interdental space will comprise pushing the string 4 like a dental floss through the contact point 14 between the teeth 2 defining the interdental space 5, as shown in FIGS. 2 and 3 of the drawing. The dotted line illustrate the position of string 4 at the end of said first step.

The second container means 9 may also be a separate unit provided with a ring or a string 10 at one end, which ring or string 10 is intended to be attached to the string 4 of the first container means 3 e.g. by means of a knot or the like, when said string 4 has been pushed through the contact point 14 into the interdental space 5 or threaded through the interdental space 5 adjacent a tooth 2 to be treated, and the first container means 3 has been pulled into said interdental space 5.

The second container means 9 is advantageously prefilled to a predetermined thickness and resiliency with a medium 11 such as a liquid, a gas or a gel in order to seal a proximal tunnel opening when said second container means 9 has been drawn into said interdental space 5 on removing the first container means 3 from said interdental space 5, after said tunnel preparation 1 has been filled.

The medium 11 in the second container means 9 may be a photoluminiscencing medium enabling photocuring of the restorative material 6 filled into the tunnel preparation 1 by irradiation with visible light 12.

According to another embodiment the second container means 9 is provided with an axially extending, flexible and laterally lighting fiber optic 11b enabling curing, by means of lasers, plasma arc or halogen light, of the dental restorative resin 6 filled into the tunnel preparation 1 from the first container means 3.

According to a further embodiment the second container means 9 includes a triboluminicence system, i.e a first medium 11, luciferin and a luciferas capcule 11a providing chemiluminescence when said container means 9 is squeezed or bent in order to break the luciferase capsule bringing both components into contact with each other.

The second container means 9 may also be provided with a combination of chemiluminescence 11,11a and a fiber optic 11b, whereby an initial soft polymerization can be carried out by means on chemiluminescence and the final polymerization is carried out means of fiber optic.

If the flowable restorative material is a photocuring material, such as a light curable composite resin, it is prefered that the first flexible container means 3 is made of a photoblocking material, such as nylon, polyester, teflon or the like containing pigments which make the materials non-transparent for wave lengths which are used to polymerize such light curable materials. A suitable material is for instance a see through orange nylon or analogue material, which prevents photocuring as long as the restorative material is stored in the container means 3. The material of the second container means 9 should be transparent in order to enable light curing of the restorative material in the tunnel preparation 1 through said second container means.

If the restorative material 6 is self, dual or chemically curable, both the first (3) and the second (9) container device may be manufactured of a transparent nylon or an analogue transparent material.

According to one embodiment the first flexible container means 3 is substantially cylindrical and the second container means 9 is cylindrical or slightly conical, widening against the end facing away from the first container means 3.

According to a preferred embodiment both container means 3 and 9 are provided with a triangular cross section as indicated in FIGS. 20a and 21a, which shape more exactly corresponds to the shape of an interdental space 5. One longitudinal edge of the device can be provided with an outwardly extending fin 13, which is intended to be placed in the contact point 14 of the adjacent teeth 2, and will thus act as a guiding reference.

A device with a triangular cross section may be manufactured of thin monofilms such as polyester, e.g. Mylar®, Pu Pont), nylon, teflon etc. films in thickness of 12 microns and more. Also multilayer films of polyester laminated with polyethylene and polypropylene having a thickness of 40–50 microns are suitable materials for both container means 3 and 9. These materials can be heat or laser welded to form container means having a desired geometric form, such as a prisma-like container means having a triangular cross section and planar end walls or a container means having a triangular cross section and a longitudinal outstanding fin 13 along one edge, the ends of said container means being squeeze welded to form end fins 61a, 16b parallel to the longitudinal fin 13. In the device the two container means 3 and 9 are connected to each other by means of a common end fin 16b.

According to a preferred embodiment the device comprises a number of sequential container means (I–VII), as shown in FIGS. 21 and 21a, having a triangular cross section and connected to each other by means of common end fins 16b. The device is provided with a longitudinal outstanding fin 13 extending along the whole length of the device. The end fin 16a in the front end of the device is provided with a string 4 to facilitate the insertion of the device into an interdental space 5 and the device is then intended to be pulled step by step through the interdental space 5. The longitudinal fin 13 is provided with text indicating the purpose of each container means. In the shown embodiment the first container means I contains an etching gel intended for conditioning a tunnel prepartion 1 in a tooth 2 for 15 seconds, as indicated at the fin 13. The etching gel is intended to enter the tunnel preparation 1 through a hole 7 punched in said container means I for instance by means of a needle 8 as shown in FIG. 21b, brought into contact with said container means I through said tunnel preparation 1.

Container means II contains air to be used for rinsing and drying the tunnel preparation 1. For that purpose a 3-ways syringe 17 as that shown in FIG. 21b can be used. By usind such a 3-ways syringe 17 two holes 7 and 7a have to be punched in said container means II, one hole 7 facing to the tunnel preparation and one hole 7a for inserting the needle 8 of said 3-ways syringe, through which rinsing liquid and drying air can be fed into said container means II and further into the tunnel preparation 1. Thus rinsing and drying and other treatments can be carried out from the interdental space 5 towards the occlusal surface of the tooth 2. Container means III is filled with a prime & bonding agent which then is fed into the tunnel preparation 2 through a hole 7 punched in the wall of said container means III in the same way as described above. The prime & bonding agent is allowed to react in the tunnel preparation for 20 seconds. Then container means IV containing air is pulled into the interdental space 5 and drying is carried out as described in connection with container means II for 5 seconds, after which container means V, filled with air, is pulled into the interdental space 5 for closing the proximal opening during the light curing of the prime & bonding agent for 10 seconds. Container means VI containing a flowable restorative material is then pulled into the interdental space 5 and a hole 7 is punched as described above and the flowable restorative material 6 is pressed from the container means VI into the tunnel preparation 1 until it is completely filled, after which container means VII containing air is pulled into the interdental space 5 for preventing the restorative material 6 from flowing out from the tunnel preparation 1 into the interdental space, during final light curing of the restorative material, i.e. for preventing overhangs. For pressing each material from said container means I, III and VI and for closing the proximal opening of the tunnel preparation 5 by means of the container means V and VII a special pressing tool provided with rotatable rolls which can be pressed against that container means which has been pulled into the interdental space.

According to an embodiment as shown in FIGS. 8 and 9 the opposite end of the first flexible container means 3 is laser, heat or chemically bonded to the outlet opening 18 of a cartridge 19, filled with said flowable restorative material 6. Said cartridge 19 is adaptable to an applicator device 20, for instance a pistol like applicator device of Centrix Inc. The outlet opening 18 communicates with the cavity of said first container means 3, which in this embodiment is in a vacuumized, thin and flat condition before use.

According to a prefered embodiment of the invention the closed end of said first flexible container means 3 is attached, preferably by means of a string 4 or a seam to an end of a second closed and flexible container means 5.

The device can be also be provided with a separate longitudinal closed and flexible second container means 9, one end of which is provided with a string 10, which is intended to be threaded through an interdental space 5 from one side before the string 4 of the first container means 3 is threaded into the same interdental space (5) from the opposite side. The cartridge 19 or the applicator device 20, is provided with a hook 21 or similar device, to which the string 10 of the second container means 9 can be hooked, so that the second container device is pulled into the interdental space 5 simultaneously as the first container means is removed from said interdental space 5, as will appear from FIGS. 10, 11, 12, 13b and 14.

The string 10 of the second container means 9 can also be attached to the string 4 of the first container means 3 when the first container means 3 has been pulled into an interdental space 5, which also have been shown in FIG. 12, FIG. 13a and FIG. 14.

If the restorative material 6 in the cartridge 19 is of a light curable type the cartridge 19 should be photoblocked, preferably by using a see through orange plastics or a 100% photoblock material for manufacturing the cartridge 19.

The use of a device according to the invention is described below step by step.

A lesion and its relation to anatomic structures of a tooth 2 is located by means of a preoperative radiological digital image.

The affected tooth 2 is anesthetized.

After the placement of a rubber dum interdental accessories such as Wedjets dam cord as color indicator, fiber optic illumination and a metal matrix piece are used to guide and protect during the preparation procedure.

An occlusal access preparation 1 is made into center fissure of the tooth 2 with a high speed, water-cooled bur or by means of air-abrasive technology, i.e. kinetic cavity preparation.

In the fiber optic illumination bright yellow or red interdental cord (Wedjets) glimmer through the enamel guiding the operator to remove approximal caries but saving as much as possible of the intact enamel. Aim is to pass the bur underneath the contact point 14 between the damaged tooth 2 and an adjacent tooth through the enamel, just there where caries penetrated into the tooth 2. The interdental matrix band will protect the adjacent tooth.

Caries removal is verified e.g. by caries detector, using hand-instrument probing, suitable rotary instruments and/or carisolv system in direct vision preferably under an operating microscope with bright illumination and magnification. However, microscope is only an option and is not necessarily needed.

Enamel margins of approximal and occlusal openings are finished by suitable diamond or tungsten carbide burs.

Wedjet dam cord and matrix band are removed.

Smear layer is removed with air-water spray and then the tooth is gently dried by stream of warm air. If the multifunctional device shown in FIG. 21 is used it is pulled into the interdental space 5 before this stage, and the treatment is continued as previously described.

Tunnel-cavity is "primed" to receive filling material following the instructions of the manufacturer (primer/conditioner/etch gel/bonding resin-system).

If for instance a device shown in FIG. 1 is to be used, it is at this stage placed interdentally as previously described by pressing the string 4 as a dental floss through the contact point 14 from occlusal access and then pulling the first contained means 3 into the interdental space. The first container means is now squeezed by means of a hemostat or the like in order to adapt said first container means 3 tightly on the approximal surfaces below the contact point 14 of the two adjacent teeth 2. The first container means 3 will now tightly cover the approximal opening of the prepared tunnel cavity 1. If a device according to FIG. 8 or 9 is to be used the first container means 3 of it is pulled into the interdental space 5 in a flat and empty condition. The restorative material 6 in the cartridge 19 is then pressed by an applicator device 20 into the first flexible container means 3, which fills up and adapts itself tightly on the approximal surfaces below the contact point of the two adjacent teeth.

The operator punches from the occlusal access through the prepared tunnel 1 a small hole 7 into the first flexible container means 3 with a suitable needle 8 (analogue to an endoinstrument). By maintaining a constant pressure inside the first flexible container means 3 by using the hemostat 15 or by pressing the applicator device 20, the flowable restorative material 6 will flow slowly from the first flexible container 3 into the tunnel 1 through the approximal access.

The tunnel cavity 1 is then slowly filled by the restorative material 6 under bear eye control. As soon the material 6 has reached the margins of the occlusal cavity the pressure is released. The device is then pulled laterally until the first flexible container means 3 is pulled out from the interdental space and the second flexible container means 9 takes its place, which preferably is prefilled to a predetermined thickness and resiliency with a resilient and medium 11. The second container means 9 is then squeezed by means of the hemostat 15, so that said contaimer means 9 seals tightly the approximal opening of the filled tunnel cavity 1. While said second container means 5 is maintained pressurized the filling material is polymerized e.g. by using a three sited (partly trans enamel) light curing technique, utilizing any of the second container means 9 disclosed in FIGS. 15 to 19. The curing time per site is 60 seconds or shorter. By using argon laser a curing time of 7.5 seconds or even less per site may be sufficient.

The second flexible container device is then depressurized and removed by further pulling the whole device laterally away.

The occlusal surface of the tooth is then adjusted and polished. A fluoride solution, varnish, gel etc. is applied occlusally and interdentally. Due to the device according to the invention the approximal surface needs no checking for overhangs and marginal imperfections.

What is claimed is:

1. A device for filling and reinforcing an internal tunnel in a tooth from which tooth approximal caries has been removed by means of a tunnel preparation, comprising:

a closed first elongate and flexible container means having one end provided with a string to enable insertion of said first container means into an interdental space adjacent the portion of said tooth, from which approximal caries has been removed, said first container means being prefilled with a flowable restorative material, which is disposed to flow into and fill said tunnel preparation when a hole has been punched into said first container means.

2. A device according to claim 1, wherein:

the fast flexible container means is made of photoblocking nylon.

3. A device for filling and reinforcing an internal tunnel in a tooth from which tooth approximal caries has been removed by means of a tunnel preparation and for preventing overhangs, comprising:

a closed full elongate and flexible container means having one end provided with a tip or string to enable insertion of said first container means into an interdental space adjacent the portion of said tooth, from which approximal caries has been removed, wherein said closed first container means is prefilled to about 60 to 80% of its volume with a flowable restorative which is disposed to flow into and fill said tunnel preparation when a hole has been punched into said first container means.

4. A device for filling and reinforcing an internal tunnel in a tooth from which tooth approximal caries has been removed by means of a tunnel preparation, comprising:

a closed first elongate and flexible container means having one end provided with a string to enable insertion of said first container means into an interdental space adjacent the portion of said tooth, from which approximal caries has been removed; and a second closed and flexible container means attached to the device;

said first container means being prefilled with a flowable restorative material, which is disposed to flow into and fill said tunnel preparation when a hole has been punched into said first container means.

5. A device according to claim 4, wherein:

the second container means is attached to the string of the first flexible container means.

6. A device according to claim 5, wherein:

the second container means is attachable to the string of the first container means by means of a ring or a string mounted to one end of said second container means, when said first container means has been pulled into an interdental space adjacent a tooth from which approximal caries has been removed.

7. A device according to claim 4, wherein:

the second container means is prefilled to a predetermined thickness and resiliency with a medium comprising at least one of, a gas or a gel in order to seal a proximal tunnel opening when said second container means has been drawn into said interdental space on removing the first container means from said interdental space after said tunnel preparation has been filled.

8. A device according to claim 7, wherein:

said medium is a photoluminiscencing medium enabling photocuring of the dental restorative resin filled into the tunnel preparation by irradiation with visible light.

9. A device according to claim 7, wherein:

the second container means is provided with an axially extending, flexible and laterally lighting fiber optic, wherein the fiber optic is arranged to cure by means of lasers, plasma arc or halogen light, a dental restorative resin filled into a tunnel preparation from said first container means.

10. A device according to claim 6, wherein:

said second container means includes a triboluminicence system comprising luciferin and a luciferase capsule, wherein the tribolumimcence system provides chemiluminescence when said container means is squeezed or bent breaking said luciferase capsule and bringing lucifirin and luciferase into contact with each other.

11. A device according to claim 7, wherein:

said second container includes a combination of chemiluminescence and a fiber optic.

12. A device according to claim 4, wherein:

the first and the second flexible container means are made of transparent nylon or analogue transparent material.

13. A device according to claim 4, wherein:

the first flexible container means is substantially cylindrical and the second flexible container means is cylindrical or slightly conical, widening against the end facing away from the first container means.

14. A device according to claim 4, wherein:

both flexible container means are provided with a triangular cross section and having one edge provided with a longitudinal outstanding fin.

15. A device according to claim 14, wherein:

the ends of the container means are squeeze welded to form end fins parallel to the longitudinal fin of said container means, one end fin of each container means being common to both container means.

16. A device according to claim 15, wherein:

the device comprises a number of sequential container means, connected to each other by common end fins, the end fin in the front end of said device being provided with a string to facilitate insertion of said device into an interdental space, and the longitudinal fin being provided with indications of the purpose of each container means, which container means are intended to be pulled step by step into the interdental space.

17. A device for filling and reinforcing an internal tunnel in a tooth from which tooth approximal caries has been removed, comprising:

a closed first elongate and flexible container having means for inserting the first container into an interdental space between two adjacent teeth, said first container means being prefilled with a flowable restorative material which is disposed to flow into and fill a tunnel preparation when a hole has been punched into said first container means.

18. A device according to claim 17, comprising:

a second closed and flexible container connected to the means for enabling insertion.

19. A device according to claim 18, wherein:

the second container means is prefilled to a predetermined thickness and resiliency with a medium comprising at least one of a gas or a gel.

20. A device according to claim 19, wherein:

said medium is a photoluminisceing medium enabling photocuring of a dental restorative resin filled into the tunnel preparation by irradiation with visible light.

21. A device according to claim 18, wherein:

the second container means is provided with an axially extending, flexible and laterally lighting fiber optic, wherein the fiber optic is arranged to care by means of lasers, plasma arc or halogen light, a dental restorative resin filled into a tunnel preparation from said first container means.

22. A device according to claim 18, wherein:

said second container means includes a triboluminicence system comprising luciferin and a luciferase capsule, wherein the triboluminicence system provides chemiluminescence when said container means is squeezed or bent breaking said luciferase capsule and bringing lucifern and luciferase into contact with each other.

23. A device according to claim 18, wherein:

said second container includes a combination of chemiluminescence and a fiber optic.

24. A device according to claim 18, wherein:

the first and the second flexible container means are made of transparent nylon or analogue transparent material.

25. A device according to claim 18, wherein:

the first flexible container means is substantially cylindrical and the second flexible container means is cylindrical or slightly conical, widening against the end facing away from the first container means.

26. A device according to claim 18, wherein:

both flexible container means are provided with a triangular cross section and having one edge provided with a longitudinal outstanding fin.

27. A device according to claim 26, wherein:

the ends of the container means are squeeze welded to form end fins parallel to the longitudinal fin of said container means, one end fin of each container means being common to both container means.

28. A device according to claim 27, wherein:

the device comprises a number of sequential container means, connected to each other by common end fins, the end fin in the front end of said device being provided with a string to facilitate insertion of said device into an interdental space, and the longitudinal fin being provided with indications of the purpose of each container means, which container means are intended to be pulled step by step into the interdental space.

29. A device according to claim 17, wherein:

the first flexible container means is made of photoblocking nylon.

* * * * *